US 9,279,793 B2

(12) United States Patent
Powell

(10) Patent No.: US 9,279,793 B2
(45) Date of Patent: Mar. 8, 2016

(54) ANTENNA INSTALLATIONS

(75) Inventor: Stephen Charles Powell, Lee-on-the-Solent (GB)

(73) Assignee: BAE SYSTEMS PLC, London (GB)

( * ) Notice: Subject to any disclaimer, the term of this patent is extended or adjusted under 35 U.S.C. 154(b) by 186 days.

(21) Appl. No.: 14/342,708

(22) PCT Filed: Sep. 5, 2012

(86) PCT No.: PCT/GB2012/052175
§ 371 (c)(1),
(2), (4) Date: Mar. 4, 2014

(87) PCT Pub. No.: WO2013/034901
PCT Pub. Date: Mar. 14, 2013

(65) Prior Publication Data
US 2014/0203996 A1 Jul. 24, 2014

(30) Foreign Application Priority Data
Sep. 5, 2011 (GB) .................................. 1115271.7

(51) Int. Cl.
G01B 1/00 (2006.01)
G01N 33/00 (2006.01)
G08B 21/20 (2006.01)
G01F 1/00 (2006.01)

(52) U.S. Cl.
CPC .............. G01N 33/0004 (2013.01); G01F 1/00 (2013.01); G08B 21/20 (2013.01)

(58) Field of Classification Search
CPC ......... H01Q 1/1278; H01Q 1/02; H01Q 1/32; H01Q 1/42
USPC ................................................. 343/704, 894
See application file for complete search history.

(56) References Cited

U.S. PATENT DOCUMENTS

| 5,798,735 A * | 8/1998 | Walton, Jr. ............... H01Q 1/02 343/704 |
| 5,861,855 A * | 1/1999 | Arsenault .............. H01Q 19/12 343/703 |
| 5,945,955 A * | 8/1999 | Glover .................... H01Q 1/02 343/704 |
| 6,172,647 B1 * | 1/2001 | Jones .................... E04D 13/103 219/213 |

(Continued)

FOREIGN PATENT DOCUMENTS

| DE | 4127179 A1 | 2/1993 |
| JP | 61059252 A | 3/1986 |

(Continued)

OTHER PUBLICATIONS

International Search Report received for Patent Application No. PCT/GB2012/052175, mailed on Nov. 2, 2012, 2 pages.

(Continued)

Primary Examiner — Linh Nguyen
(74) Attorney, Agent, or Firm — Finch & Maloney PLLC

(57) ABSTRACT

An antenna installation comprises a plurality of antenna assemblies (10) mounted in respective enclosures (12). The enclosures are interconnected by flow connections (14) allowing passage of dry air supplied from a dry air panel (16). Having passed through all the enclosures, the dry air exhausts through a dry air return (18). The dew point of the air in the dry air return is detected by a dew point sensor (22). An air flow sensor (24) is disposed downstream of the dew point sensor and signals alarm if the air flow falls below a preset threshold.

5 Claims, 1 Drawing Sheet

(56) References Cited

U.S. PATENT DOCUMENTS

| | | | |
|---|---|---|---|
| 6,326,930 B1* | 12/2001 | Jones | H01Q 1/02 343/704 |
| 6,445,349 B1* | 9/2002 | Jones | H01Q 1/02 343/704 |
| 7,381,245 B2 | 6/2008 | Fleischer | |
| 2007/0165353 A1* | 7/2007 | Fleischer | A61L 9/22 361/212 |
| 2008/0104987 A1 | 5/2008 | Carlsen et al. | |
| 2010/0328167 A1* | 12/2010 | Stephens | H01Q 1/02 343/704 |
| 2011/0139011 A1* | 6/2011 | Jones | B01D 46/46 96/173 |
| 2011/0273344 A1* | 11/2011 | Reams | H01Q 19/13 343/704 |
| 2015/0135827 A1* | 5/2015 | Benz | H01Q 1/02 73/290 V |

FOREIGN PATENT DOCUMENTS

| | | |
|---|---|---|
| JP | 08082432 A | 3/1996 |
| JP | 08274519 A | 10/1996 |
| JP | 2004193855 A | 7/2004 |
| WO | 2013034901 A1 | 3/2013 |

OTHER PUBLICATIONS

GB Intellectual Property Office Search Report under Section 17(5) received for GB Patent Application No. 1115271.7. date of search Dec. 12, 2011, 1 page.

International Preliminary Report on Patentability and Written Opinion of the International Searching Authority received for Patent Application No. PCT/GB2012/052175, mailed on Mar. 20, 2014, 4 pages.

* cited by examiner

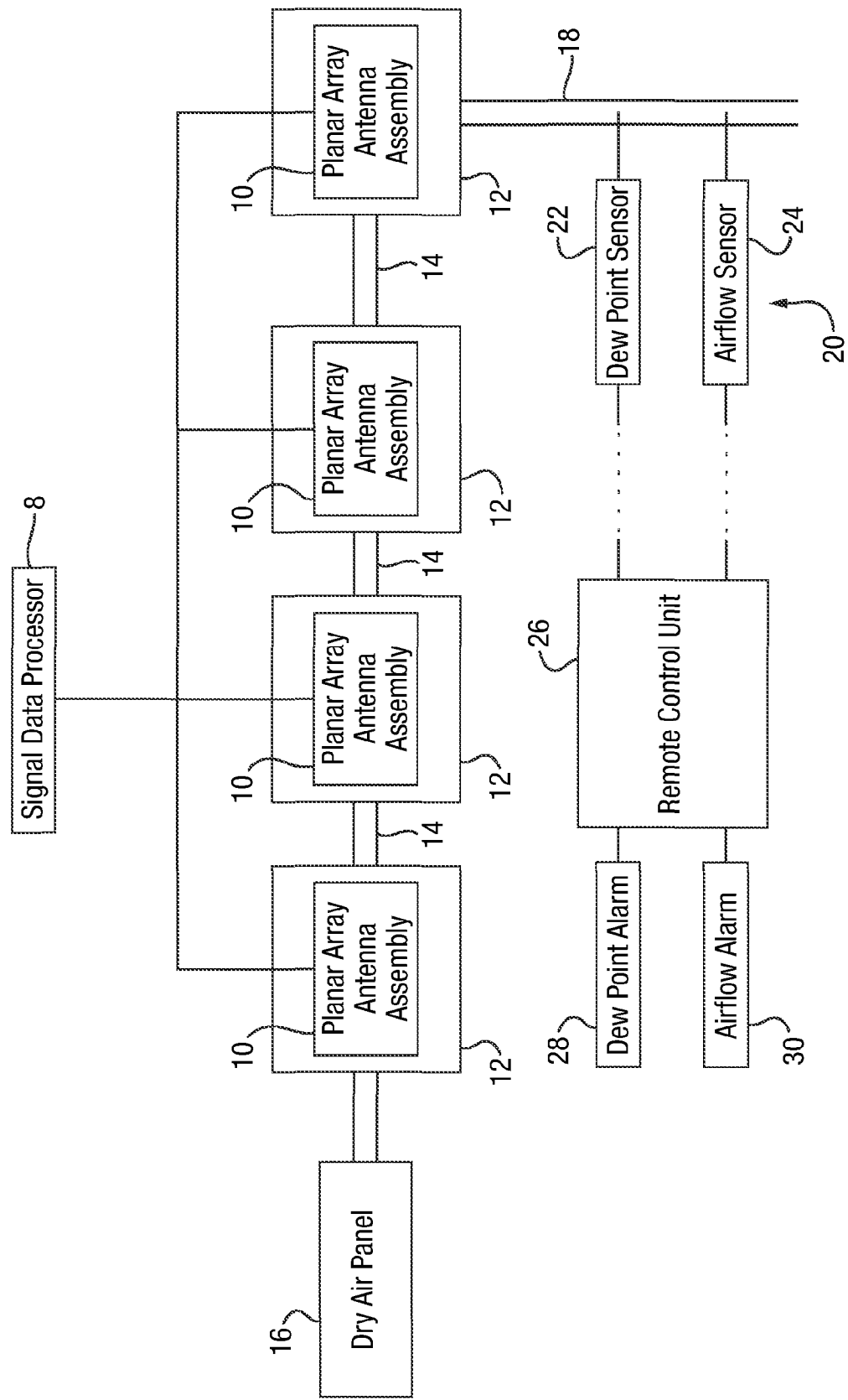

ANTENNA INSTALLATIONS

This invention relates to antenna installations and, in particular but not exclusively, to antenna installations including one or more antenna arrays, each located in an enclosure each provided with a controlled environment. In typical such installations on board a ship, a dry air panel provides dry air to the enclosures. The dry air panel is designed to ensure that the temperature and humidity of the air or the atmosphere within the environment lie within specific ranges to ensure effective operation of the antenna array in use. The term dry air is used broadly to mean air whose humidity is controlled to be below a predetermined limit. It is known to provide a system where the atmosphere within the sealed environment is sampled and passed to a dew point sensor which determines the dew point of the atmosphere and generates an alarm if the dew point passes a given threshold. Although such a system is effective, we have found that there is a potential problem if for any reason the dew point sensor is not supplied with an air sample because under these conditions the dew point sensor may give an erroneous signal and mask the fact that the atmosphere within the enclosures has deteriorated beyond the operating requirements.

Accordingly, in one aspect, this invention provides a sensor arrangement for an antenna installation which includes an antenna array located in an enclosure which is supplied with conditioned atmosphere supplied directly or indirectly from a dry air source, the sensor arrangement including a dew point sensor disposed in a flow path away from said enclosure, adapted to detect the dew point of atmosphere passing along said flow path, and an air flow sensor adapted to monitor flow along said flow path and to generate an alarm if said air flow falls below a predetermined threshold.

Preferably said air flow sensor provides a flow/no flow output signal.

Preferably said air flow sensor is located in the flow path downstream of said dew point sensor.

In one arrangement, the antenna installation may include a series of antenna arrays each in a respective enclosure, with a first one of said enclosures receiving air from said dry air source, with connecting flow passages provided between adjacent enclosures, and the dew point sensor and the air flow sensor being disposed in a flow path away from the final enclosure in the series.

According to another aspect, this invention provides an antenna installation including an antenna array located in an enclosure which is supplied with conditioned atmosphere supplied directly or indirectly from a dry air source, a sensor arrangement including a dew point sensor disposed in a flow path away from said enclosure, adapted to detect the dew point of atmosphere passing along said flow path, and an air flow sensor adapted to monitor flow along said flow path and to generate an alarm if said air flow falls below a predetermined threshold.

Whilst the invention has been described above, it extends to any inventive combination or sub-combination of novel features disclosed above or set out in the following description, drawing or claims.

The invention may be performed in various ways and, by way of example only, an embodiment thereof will now be described, reference being made to the accompanying drawing which is a schematic diagram of an antenna installation including a remote sensor in accordance with this invention.

Referring to the drawing, a ship-borne antenna installation is illustrated comprising four planar array antenna assemblies 10 mounted in respective enclosures 12. The planar array antenna assemblies 10 are supplied with transmission signals and control signals from a signal data processor 8.

Adjacent enclosures are linked by flow connections 14 which allow air flow between the enclosures. Dry air supplied from a dry air panel 16 to a first enclosure 12 and then passes successively through the flow connections 14 to the last enclosure in the series. From the last enclosure the air 12 passes along a dry air return 18, eventually to vent to atmosphere. Before venting, the air passes to a sensor sampling system 20, comprising a dew point sensor 22 and downstream thereof an air flow sensor 24. The dew point sensor 22 and the air flow sensor 24 provide signals to a remote control unit 26. The dew point sensor 22 is selected to signal an alarm to said remote control unit 26 if the dew point temperature falls below a preset value in the range of from −100° C. to +20° C. which is displayed on a dew point alarm 28. Likewise, the air flow sensor 24 signals an alarm if the air flow rate is nil or drops below a preset threshold, with the alarm being displayed on an air flow alarm 30.

The invention claimed is:

1. A sensor arrangement for an antenna installation which includes an antenna array located in an enclosure which is supplied with conditioned atmosphere supplied directly or indirectly from a dry air source, the sensor arrangement including a dew point sensor disposed in a flow path away from said enclosure, adapted to detect the dew point of atmosphere passing along said flow path, and an air flow sensor adapted to monitor flow along said flow path and to generate an alarm if said air flow falls below a predetermined threshold.

2. A sensor arrangement according to claim 1, wherein said air flow sensor provides a two state flow/no flow output signal.

3. A sensor arrangement according to claim 1, wherein said air flow sensor is located in the flow path downstream of said dew point sensor.

4. A sensor arrangement according to claim 1, wherein the antenna installation includes a series of antenna arrays each in a respective enclosure, with a first one of said enclosures receiving air from said dry air source, with connecting flow passages provided between adjacent enclosures, and the dew point sensor and the air flow sensor being disposed in a flow path array from the final enclosure in a series.

5. An antenna installation including an antenna array located in an enclosure which is supplied with conditioned atmosphere supplied directly or indirectly from a dry air source, a sensor arrangement including a dew point sensor disposed in a flow path away from said enclosure, adapted to detect the dew point of atmosphere passing along said flow path, and an air flow sensor adapted to monitor flow along said flow path and to generate an alarm if said air flow falls below a predetermined threshold.

* * * * *